United States Patent
Verswyvel et al.

(10) Patent No.: US 11,891,503 B2
(45) Date of Patent: *Feb. 6, 2024

(54) NON-STICKY, SOFT AND TRANSPARENT STYRENIC THERMOPLASTIC ELASTOMERS

(71) Applicant: INEOS STYROLUTION GROUP GMBH, Frankfurt am Main (DE)

(72) Inventors: Michiel Verswyvel, Mechelen (BE); Norbert Niessner, Friedelsheim (DE); Eike Jahnke, Aubonne (CH); Daniel Wagner, Bad Duerkheim (DE); Konrad Knoll, Mannheim (DE)

(73) Assignee: INEOS STYROLUTION GROUP GMBH, Frankfurt am Main (DE)

( * ) Notice: Subject to any disclaimer, the term of this patent is extended or adjusted under 35 U.S.C. 154(b) by 252 days.

This patent is subject to a terminal disclaimer.

(21) Appl. No.: 16/494,098

(22) PCT Filed: Mar. 12, 2018

(86) PCT No.: PCT/EP2018/056026
§ 371 (c)(1),
(2) Date: Sep. 13, 2019

(87) PCT Pub. No.: WO2018/166950
PCT Pub. Date: Sep. 20, 2018

(65) Prior Publication Data
US 2022/0267584 A1    Aug. 25, 2022

(30) Foreign Application Priority Data
Mar. 16, 2017 (EP) ..................... 17161331

(51) Int. Cl.
*C08L 53/02* (2006.01)
*A61M 39/00* (2006.01)
*C08F 297/04* (2006.01)
*C08L 91/00* (2006.01)

(52) U.S. Cl.
CPC ............. *C08L 53/02* (2013.01); *A61M 39/00* (2013.01); *C08F 297/044* (2013.01); *C08L 91/00* (2013.01); *C08L 2203/02* (2013.01); *C08L 2207/04* (2013.01)

(58) Field of Classification Search
CPC ...... C08L 53/02; C08L 91/00; C08L 2203/02; C08L 2207/04; C08F 297/044; A61M 39/00
See application file for complete search history.

(56) References Cited

U.S. PATENT DOCUMENTS

| | | |
|---|---|---|
| 6,031,053 A | 2/2000 | Knoll et al. |
| 6,197,889 B1 | 3/2001 | Knoll et al. |
| 6,521,712 B1 | 2/2003 | Knoll et al. |
| 6,593,430 B1 | 7/2003 | Knoll et al. |
| 6,673,857 B1 | 1/2004 | Knoll et al. |
| 11,066,503 B2 * | 7/2021 | Verswyvel .............. A61L 29/06 |
| 2009/0286918 A1 | 11/2009 | Stewart et al. |
| 2014/0011929 A1 | 1/2014 | Knoll et al. |

FOREIGN PATENT DOCUMENTS

| | | | | |
|---|---|---|---|---|
| WO | WO-9909081 A1 * | 2/1999 | ............ | C08F 279/02 |
| WO | 2012/055919 A1 | 5/2012 | | |
| WO | 2012/084914 A1 | 6/2012 | | |

* cited by examiner

*Primary Examiner* — John E Uselding
(74) *Attorney, Agent, or Firm* — RAPHAEL BELLUM PLLC

(57) ABSTRACT

Thermoplastic elastomer compositions can be use for medical applications, Comprising: a) 97.1 to 90.9 wt.-% star-shaped block copolymer A with identical arms of the structure $[S_1\text{-}(S/B)_k\text{-}(S/B)_l\text{-}(S/B)_m\text{-}S2]_n\text{-}X$, where $S_1$ and $S_2$ are vinylaromatic hard polymer and S/B are soft random vinylaromatic/diene copolymer blocks; X is a coupling center; and b) 2.9 to 9.1 wt.-% plasticizer B.

17 Claims, No Drawings

NON-STICKY, SOFT AND TRANSPARENT STYRENIC THERMOPLASTIC ELASTOMERS

The invention relates to non-sticky, soft and transparent styrenic thermoplastic elastomers (S-TPE), thermoplastic elastomer compositions comprising said elastomers, the processes for their preparation, shaped articles produced therefrom, and the use of said S-TPE composition, in particular for medical applications, in particular medical tubings and bags.

Common thermoplastic elastomers used for medical applications, such as plasticized PVC have several disadvantages. When joining soft medical tubes made from PVC with fittings made from stiff styrenic polymers, often plasticizer migration from the PVC parts into the styrenic parts occurs. This migration destroys the plastic properties and results in reduced environmental stress-cracking resistance. Thus, there is a need for improved materials which are suitable for medical applications.

U.S. Pat. Nos. 6,031,053 and 6,197,889 disclose elastomeric linear and star-shaped SBC block copolymers i.a. of the general formula Y-[(A-B/A)$_n$-A]$_{m+1}$ and Y-[(B/A-A)$_n$]$_{m+1}$ where A is a vinylaromatic block forming a hard phase, B/A is a random diene/vinylaromatic copolymer block forming a soft phase, Y is a radical of a coupling agent, m and n are 1 to 10. Examples show coupled star shaped block copolymers of the structure Y-[(B/A)-(B/A)-(B/A)-A] having a molecular weight Mw of 175000 g/mol or 145000 g/mol.

WO 2012/055919 describes star-shaped elastomeric SBC block copolymers having at least 2 different arms and mixtures thereof. Preferred are coupled block copolymers having 3 or 4 arms—having a hard-soft-hard-soft-hard pentablock character—of the general formula [A1-B/A-A2-]$_m$[A2-]$_l$Y where A1 and A2 are vinylaromatic hard blocks (A1 greater than A2) and B/A is a soft vinylaromatic/diene copolymer block. The total mass Mw of the block copolymers is preferably 120000 to 200000 g/mol.

U.S. Pat. No. 6,673,857 discloses a thermoplastic elastomer composition comprising 5 to 99 wt.-% of a SBC block copolymer and 1 to 95 wt.-%, preferably 4 to 49 wt.-%, of a plasticizer based on vegetable oil or its mixture with white oil. The SBC block copolymer is a symmetrical three-block copolymer or a star block copolymer with outer blocks S and random soft blocks B/S lying therebetween (no examples). The diene content of the block copolymer is less than 50 wt.-% and the proportion of the soft phase is at least 60 wt.-%. Compositions with linear S-B/S-S block copolymers (Mw 163000 g/mol) and 5 or 10 wt.-% of a white oil/sunflower oil mixture (40/60) have a shore A hardness of 68 or 63 and a high melt flow index (5 kp, 10 min$^{-1}$) of 16.9 or 27.8 at 180° C.

These thermoplastic elastomer compositions leave something desired in terms of their processability in particular for extrusion purposes.

WO 2012/084914 describes thermoplastic elastomer compositions comprising a) 5% to 99 wt.-% of a block copolymer synthesized from hard blocks A of vinylaromatic monomers and one or more random soft blocks B of diene/vinylaromatic copolymers, and b) 1% to 95 wt.-% of a plasticizer, in particular mixtures of diisononyl cyclohexane-1,2-dicarboxylate (DINCH) with white oil. The block copolymer is preferably a symmetrical triblock copolymer with external blocks A and an inner block B. Said triblock copolymer is able to absorb up to 10 wt.-% of white oil without bleeding.

With said DINCH/white oil combination the oil uptake could be increased and the softness improved, but the material performs not well enough regarding mechanical properties. For example, in particular for tubing applications, the snappiness or kinking behavior, i.e. the recovery from bending, is still in need of improvement.

One object of the invention is to provide transparent and soft S-TPEs which—in comparison to prior art S-TPE—have an improved oil-uptake without deterioration of their mechanical properties and show a non-sticky behavior. A further object is to provide a S-TPE composition which has an improved snappiness or kinking behavior. One further object of the invention is that S-TPEs with the aforementioned properties are provided which can be produced in a high space-time yield. One further object of the invention is to provide a S-TPE composition which maintains a good processability—identified by a melt volume flow rate (MFI$_{200/5}$) of 16 cm$^3$/10 min or less—when increasing amounts of plasticizers are added.

Subject of the invention is a thermoplastic elastomer composition comprising (or consisting of) components a), b) and c):

a) 97.1 to 90.9 wt.-% of at least one star-shaped block copolymer A of the structure

$$[S_1(S/B)_k\text{-}(S/B)_l\text{-}(S/B)_m\text{-}S_2]_n\text{-}X \qquad (I),$$

where $S_1$ and $S_2$ are polymer blocks made from at least one vinylaromatic monomer and S/B are random copolymer blocks made from at least one vinylaromatic monomer and at least one diene forming a soft phase; X is a coupling center derived from a polyfunctional (di- or multifunctional) coupling agent;

b) 2.9 to 9.1 wt.-% of at least one plasticizer B, preferably mineral oil; and c) 0 to 2 wt.-% of further additives C;

wherein the sum of components a), b) and c) is 100 wt.-%;
the arms $S_1\text{-}(S/B)_k\text{-}(S/B)_l\text{-}(S/B)_m\text{-}S_2$ are identical;
the proportion of the blocks $S_1$ and $S_2$ (forming a hard phase), based on the entire block copolymer A, is from 24 to 40 wt.-%;
the vinylaromatic monomer/diene (=S/B) ratio of all of the blocks (S/B) is from 1/0.45 to 1/2.5;
the S/B-ratio of the blocks $(S/B)_k$, $(S/B)_l$ and $(S/B)_m$ is different from each other; the S/B-ratio of the blocks $(S/B)_k$ and $(S/B)_m$ is lower than the S/B-ratio of the block(s) $(S/B)_l$;
the weight ratio of blocks S2/S1 is from 0.1 to 0.8; and
the weight average molar mass $M_w$ (determined by GPC according to ISO 16014-3:2012) of the block copolymer A is from 200000 to 350000 g/mol; n is a natural number from 1 to 8; k, m are 1; and l is a natural number of at least 1.

The melt volume flow rate (=MFI, measured on a polymer melt at 200° C. and 5 kg load according to ISO 1133-1:2011) of the thermoplastic elastomer composition according to the invention preferably is in the range of from 8 to 16 cm$^3$/10 min, more preferably in the range of from 8 to 15 cm$^3$/10 min.

The Shore A hardness of the thermoplastic elastomer composition according to the invention—determined in accordance with ASTM D2240 (measurement after 15 seconds)—is generally in the range of from 70 to 80.

"High space-time yield" means the time between the addition of the first monomer until the addition of the terminator is 3.5 or less hours.

In the context of the invention, the average molar mass Mw is determined by GPC according to ISO 16014-3:2012

(Low T<60° C. size exclusion with relative calibration method against polystyrene standards in THF).

Wt.-% means percent by weight.

In the context of the invention "diene" means a conjugated diene. Butadiene means 1,3-butadiene.

If in the thermoplastic elastomer composition according to the invention optional component (c) is present, its minimum fraction is customarily 0.01 wt.-%.

Preferably the thermoplastic elastomer composition comprises (or consists of) components a), b) and c) in the following amounts:
a) 96.2 to 91.7 wt.-%;
b) 3.8 to 8.3 wt.-%;
c) 0 to 2 wt.-%.

More preferably the thermoplastic elastomer composition comprises (or consists of) components a), b) and c) in the following amounts:
a) 96.19 to 91.69 wt.-%;
b) 3.80 to 8.30 wt.-%;
c) 0.01 to 1.00 wt.-%.

The thermoplastic elastomer composition according to the invention preferably comprises as component a) one star-shaped block copolymer A.

The thermoplastic elastomer composition according to the invention preferably comprises as component b) one plasticizer B.

Preferably the thermoplastic elastomer composition according to the invention consists of components a), b) and c).

A further subject of the invention is the novel star-shaped block copolymer A used as component a) in the thermoplastic elastomer composition according to the invention described above.

Component a)

Star-shaped block copolymer A is of the structure:

$$[S_1\text{-}(S/B)_k\text{-}(S/B)_l\text{-}(S/B)_m\text{-}S_2]_n\text{-}X \qquad (I),$$

where $S_1$ and $S_2$ are polymer blocks made from at least one, preferably one, vinylaromatic monomer and S/B are random copolymer blocks made from at least one, preferably one, vinylaromatic monomer, and at least one, preferably one, diene, forming a soft phase; X is a coupling center derived from a polyfunctional coupling agent; wherein the arms $S_1\text{-}(S/B)_k\text{-}(S/B)_l\text{-}(S/B)_m\text{-}S_2$ are identical;

the proportion of the blocks $S_1$ and $S_2$ (forming a hard phase)—based on the entire block copolymer A—is from 24 to 40 wt.-%;

the vinylaromatic monomer/diene (=S/B) weight ratio of all of the blocks (S/B) is from 1/0.45 to 1/2.5, preferably from 1/0.50 to 1/1.2;

the S/B-ratio of the blocks $(S/B)_k$, $(S/B)_l$ and $(S/B)_m$ is different from each other; the S/B-ratio of the blocks $(S/B)_k$ and $(S/B)_m$ is lower than the S/B-ratio of the block(s) $(S/B)_l$;

the weight ratio of blocks S2/S1 is from 0.1 to 0.8; preferably 0.1 to 0.6, more preferred 0.15 to 0.40, most preferred 0.15 to 0.3; and the weight average molecular weight $M_w$ of the block copolymer A is from 200000 to 350000 g/mol, n is a natural number 1 to 8; k, m are 1; and l is a natural number of at least 1, preferably l=1 to 10, more preferably l=1, 2 or 3, most preferably l=1.

A star-shaped structure in terms of the present invention is a structure comprising 1 to 8, preferably 2 to 5, more preferably 3 to 5, most preferred 3 to 4, branches with the same sequences coupled via a linking agent, wherein each branch has the structure of a block copolymer as described above.

In the structure (I) above, n is preferably 2 to 5, more preferably 3 to 5, most preferred 3 or 4.

Further, a star-shaped structure block copolymer in terms of the present invention is a block copolymer which is obtained by forming branches of the copolymer by sequential polymerization and after that coupling the branches by addition of a suitable coupling agent, e.g. by a polyfunctional (di- or multi-functional) coupling agent. Suitable coupling agents are known to those skilled in the art and described later. The process for preparation of the inventive block copolymers is described below. As a skilled person knows it will be possible that some of the active polymer chains become terminated rather than reacting with the coupling agent.

In terms of the present invention, the block copolymer having star-shaped structure may also be a product mixture comprising star shaped structure polymers and terminated single chains.

Preferably the proportion of the blocks $S_1$ and $S_2$—based on the entire block copolymer A—is 25 to 39 wt.-%, more preferred 26 to 35 wt.-%, in particular 26 to 33 wt.-%;

Preferably the weight average molecular weight $M_w$ of the block copolymer A is from 210,000 to 320,000 g/mol, more preferably 215,000 to 300,000 g/mol.

The melt flow index (MFI) of block copolymer A according to the invention generally is in the range of from 2 to 5 cm$^3$/10 min (200° C. and 5 kg).

More preferably the vinylaromatic monomer/diene (=S/B) weight ratio of all of the blocks (S/B) is from 0.5 to 1.0, most preferably from 0.55 to 0.95.

Preferably the vinylaromatic monomer/diene (=S/B) ratio of the copolymer block $(S/B)_k$ is from 0.5 to 1, more preferably from 0.65 to 0.85.

Preferably the vinylaromatic monomer/diene (=S/B) ratio of the copolymer block(s) $(S/B)_l$ is from 0.5 to 1.2, more preferably from 0.7 to 1.1.

The soft block $(S/B)_l$ may have been subdivided into two or more random soft blocks with different molecular weights and/or different monomer compositions within the aforementioned ranges.

Preferably the vinylaromatic monomer/diene (=S/B) ratio of the copolymer block $(S/B)_m$ is from 0.3 to 0.8, more preferably from 0.4 to 0.7.

Preferably the weight average molar mass $M_w$ (determined by GPC according to ISO 16014-3:2012) of the blocks $(S/B)_k$, $(S/B)_l$ and $(S/B)_m$ is different from each other. More preferably $M_w$ of block $(S/B)_l$ is higher than $M_w$ of block $(S/B)_k$ and $M_w$ of block $(S/B)_k$ is higher than $M_w$ of block $(S/B)_m$.

Preferably the weight-average molecular weight Mw of the copolymer block $(S/B)_k$ is in the range of from 13800 to 26900 g/mol, more preferably 15700 to 25000 g/mol.

Preferably the weight-average molecular weight Mw of the copolymer block $(S/B)_l$ is in the range of from 21,200 to 41,000 g/mol, more preferably from 24,000 to 38,000 g/mol.

Preferably the weight-average molecular weight Mw of the copolymer block $(S/B)_m$ is in the range of from 11,500 to 23,000 g/mol, more preferably from 13,500 to 21,500 g/mol.

Preferably the weight-average molecular weight Mw of the polymer block $S_1$ is in the range of from 18,000 to 36,000 g/mol, more preferably from 21,600 to 34,000 g/mol.

Preferably the weight-average molecular weight Mw of the polymer block $S_2$ is in the range of from 4000 to 8100 g/mol, more preferably from 4200 to 7500 g/mol.

The vinylaromatic monomer is preferably chosen from styrene, α-methylstyrene and/or vinyltoluene, in particular styrene. The diene is preferably chosen from isoprene and/or butadiene. Particular preference is given to butadiene.

The random copolymer blocks S/B are preferably made from one vinylaromatic monomer and one diene, in particular from styrene and butadiene.

The coupling center X is formed by reaction of the living anionic polymer chain ends (=linked by way of the blocks $S_2$ with a polyfunctional (di- or multifunctional) coupling agent. Said coupling agent can generally be any suitable n- or oligo-functional compound. It is preferably selected from epoxidized vegetable oils, in particular epoxidized linseed oil or epoxidized soybean oil.

The copolymer blocks B/S composed of polymerized vinylaromatic monomers and of dienes have a random distribution. These can by way of example be obtained by anionic polymerization using alkyllithium compounds in the presence of randomizers, such as tetrahydrofuran, or potassium salts. Preference is given to use of potassium salts where the molar ratio of anionic initiator to potassium salt is in the range from 25:1 to 60:1, particularly preferably from 30:1 to 40:1. This method can at the same time achieve a low proportion of 1,2 linkages of the butadiene units. Suitable potassium salts are particularly potassium alcoholates, in particular those soluble in the polymerization solvent, e.g. tertiary alcoholates having at least five carbon atoms such as tert-amyl alcoholate or triethylcarbinolate, or other C-rich tertiary alcoholates.

The proportion of 1,2 linkages of the butadiene units is preferably in the range from 8 to 15%, based on the entirety of the 1,2, 1,4-cis, and 1,4-trans linkages.

In the case of polymers prepared anionically, the molecular weight is controlled by way of the ratio of amount of monomer to amount of initiator.

The molecular weights are usually determined by means of gel permeation chromatography (GPC) in THF as solvent, using polystyrene as standard.

The star shaped block copolymers A of the invention are produced via anionic polymerization generally in a nonpolar solvent, where the initiation process uses an initiator which is generally an organometallic compound. The production process in the invention uses addition of at least one coupling agent, generally at the end of the polymerization reaction, where the at least one initiator is added at the start of the polymerization reaction. The process of the invention permits production of the block copolymers A of the invention which in particular feature star-shaped molecular architecture with identical arms (branches) of the star.

Suitable initiators in the anionic polymerization reaction are organometallic compounds, preferably compounds of the alkali metals, particularly preferably of lithium. Examples of initiators are methyllithium, ethyllithium, propyllithium, n-butyllithium, sec-butyllithium, and tert-butyllithium. The organometallic compound is generally added in the form of solution in a chemically inert hydrocarbon. The amount added depends in principle on the desired molar mass of the polymer, but is generally from 0.002 to 5 mol %, based on the monomers.

Solvents used are preferably aliphatic hydrocarbons, such as cyclohexane or methylcyclohexane.

The anionic polymerization reaction also generally uses addition of a polar cosolvent (as randomizer), and it is believed here that the cosolvent acts as Lewis base in relation to the metal cation of the initiator. Preferred Lewis bases are polar aprotic compounds such as ethers and tertiary amines. Examples of particularly effective ethers are tetrahydrofuran and aliphatic polyethers, such as ethylene glycol dimethyl ether and diethylene glycol dimethyl ether. Tertiary amines that may be mentioned are triethylamine, tributylamine, and pyridine. The amount of the polar cosolvent added to the nonpolar solvent is by way of example from 0.5 to 5% by volume. Particular preference is given to an amount of from 0.1 to 0.6% by volume of tetrahydrofuran. An amount of from 0.2 to 0.4% by volume is very particularly preferred in many instances.

The amount added of, and the structure of, the Lewis base determine the copolymerization parameters and the proportion of 1,2- and 1,4-linkages of the diene units. The resultant block copolymers generally have a proportion of from 20 to 80% of 1,2-linkages and from 80 to 20% of 1,4-linkages, based on all of the diene units.

Preferably, a soluble potassium salt is added (as randomizer)—instead of the co-solvent—and is in particular a potassium alcoholate. It is believed here that the potassium salt interacts by metal exchange with the lithium-carbanion ion pair, thus forming potassium-carbanion compounds which preferentially form adducts with the vinylaromatic monomer, preferably styrene, whereas the lithium-carbanion compounds preferentially form adducts with the diene, particularly preferably butadiene. Since potassium-carbanion compounds are substantially more reactive, even a small fraction, namely from 1/10 to 1/50, is sufficient, together with the predominating lithium-carbanion compounds to give a similar average probability of incorporation of vinylaromatic monomers, preferably styrene, and of dienes, particularly preferably butadiene. Preference is given to use of potassium salts where the molar ratio of anionic initiator to potassium salt is in the range from 25:1 to 60:1, preferably from 30:1 to 40:1. Particularly preferably selected is a molar lithium/potassium ratio of from 33 to 39 in order to achieve approximately identical incorporation of vinylaromatic monomer, preferably styrene, and diene, preferably butadiene.

It is moreover believed that during the polymerization procedure there is frequent metal exchange between the living chains and also between a living chain and the dissolved salt, and that the same chain forms an adduct on one occasion preferentially with a vinylaromatic monomer, preferably styrene, and in turn on another occasion with a diene, particularly preferably butadiene. The resultant copolymerization parameters are then approximately the same for the vinylaromatic monomer and the diene. Suitable potassium salts are particularly potassium alcoholates, in particular those soluble in the polymerization solvent, e.g. tertiary alcoholates having at least five carbon atoms such as tert-amyl alcoholate or triethylcarbinolate, or other C-rich tertiary alcoholates.

Examples of typical corresponding alcohols are 3-ethyl-3-pentanol and 2,3-dimethyl-3-pentanol. Tetrahydrolinalool (3,7-dimethyl-3-octanol) and 2-methyl-2-butanol (tert-amylalcohol) prove to be particularly suitable. Other compounds also suitable in principle alongside the potassium alcoholates are other potassium salts which are inert toward alkyl metal compounds. Mention may be made of dialkylpotassium amides, alkylated diarylpotassium amides, alkyl thiolates, and alkylated aryl thiolates.

The polymerization temperature is generally from 0 to 100° C., preferably from 30 to 90° C., particularly preferably from 45 to 90°. The polymerization reaction is generally carried out in a plurality of stages, where the initiator is added at the start of the polymerization using a single initiation process. By way of example, the process begins by producing the hard block $S_1$. A portion of the monomers is used as initial charge in the reactor, and the polymerization reaction is initiated via addition of the initiator.

In order to achieve a defined chain structure that can be calculated from the amount of monomer and of initiator added, it is advisable to achieve high conversion (above 99%) in the process before the second monomer addition takes place. However, this is not essential.

The sequence of monomer addition depends on the selected block structure. In the case of a batch process, it is preferable to begin by using all of, or a portion of, the solvent, such as cyclohexane, as initial charge, and then to use, as initial charge, the amount of initiator, such as sec-butyllithium, that is required to establish the desired molar mass, plus what is known as a titration amount, which serves to destroy traces of impurities in the solvent and in the tank. It is then preferable to add the potassium salt, such as potassium tert-amyl alcoholate, preferably dissolved in cyclohexane, or to add the complexing solvent, such as THF to the reactor, and then to add the first amount of vinylaromatic monomer, in order to produce the block $S_1$. Diene and vinylaromatic monomer for the preparation of block $(S/B)_k$ are then added, preferably simultaneously. The addition can take place in a plurality of portions optionally together with further solvent, e.g. for improved heat dissipation, and as a function of the desired constitution. The random structure, and the constitution, of the blocks S/B are determined via the quantitative proportion of diene with respect to vinylaromatic compound, the concentration of the potassium salt, if a potassium salt is used, and the concentration and chemical structure of the Lewis base used as co-solvent, if a Lewis base is used, and also the temperature.

Then the block $(S/B)_l$ is (or sub blocks $(S/B)_{l1}$, $(S/B)_{l2}$ etc. can be) polymerized onto the growing polymer chain via addition of diene and vinylaromatic monomers. Preferably only one block $(S/B)_l$ is then polymerized onto the growing polymer chain. Then the addition of the diene and vinylaromatic monomers used for polymerizing the block $(S/B)_m$ onto the growing polymer chain takes place. At last vinylaromatic monomer is added in order to produce the block $S_2$.

According to the process of the invention, coupling with a coupling agent takes place after the last addition of vinylaromatic monomer, and the plurality of polymer blocks $S_2$ are thus bonded to one another, and the block copolymer A of the invention having star-shaped molecular architecture is formed.

It is generally possible to use any n- or oligo-functional compound as coupling agent. It is preferable that the coupling agent has been selected from epoxidized vegetable oils, such as epoxidized linseed oil or epoxidized soybean oil, silanes, such as alkoxysilanes, e.g. $Si(OMe)_4$, chlorosilanes, such as $SiCl_4$, $Si(Alkyl)_2Cl_2$, $Si(alkyl)Cl_3$, where alkyl is a $C_1$-$C_4$-alkyl moiety, preferably methyl, halides of aliphatic hydrocarbons, such as tin tetrachloride, preferred coupling agents are epoxidized vegetable oils, such as epoxidized linseed oil or epoxidized soybean oil.

The coupling agent forms the coupling center X, which is formed by reaction of the living anionic chain ends with one of the abovementioned coupling agents.

The amount of coupling agent is calculated as a function of its functionality and of the amount of initiator used. It is preferable to add the amount of coupling agent needed for reacting all of the living chains, corresponding to the amount of active initiator (total amount of initiator minus titration amount). In the case of ester groups, account has to be taken of the fact that these form two living chains, whereas in contrast epoxides and haloalkanes and -silanes form one per functional group. By way of example, epoxidized soybean oil comprises fatty acids esterified in the form of triglyceride having predominantly one or two epoxy groups, and correspondingly predominantly forms bonds with three or four polymer chains, liberating the metal alcoholate of glycerol, since the carboxy group also forms bonds with two further chains.

In the case epoxidized vegetable oils, such as epoxidized linseed oil or epoxidized soybean oil, are used as coupling agent, only approximately 70% of all living polymer chains are coupled to the coupling agent. The remaining 30% of the living polymer chains become terminated rather than reacting with the coupling agent and remain uncoupled in the polymer matrix of star shaped block copolymer A.

The polymer concentration can be varied widely, but should preferably be selected in such a way that the temperatures at the end of the polymerization reaction for the individual blocks do not exceed values of 100° C. or if they exceed that value then at most for a short time, thus avoiding any significant premature thermal termination. Typical polymer concentrations after the coupling process, in the case of a batch process in a stirred tank, are from 10 to 50% by weight, preferably from 20 to 40% by weight, and particularly preferably from 20 to 35% by weight.

Instead of a stirred tank, preferably in combination with a reflux condenser, where the internal pressure of the tank is preferably lowered to cool the reaction solution via boiling and reflux of the solvent, it is in principle also possible to use other types of reactor, for example a loop reactor in combination with a cooled section, such as a heat exchanger, or to use a stirred tank in combination with an external heat exchanger. Instead of producing the block copolymers A of the invention in a batch process, they can be produced in a continuous process via, for example, arrangement in series of the reactors listed above in various combinations, or in a tubular reactor with preferably static mixing elements, or via a combination of tubular reactor and the reactors listed above. The number of reaction zones is preferably the same as the number of different monomer additions plus the coupling agent addition.

At the start, and at the appropriate points, the initiator system, generally comprising initiator and randomizer and optionally further solvent, is additionally mixed; it is preferable here to add the solvent to the monomer feeds so that the monomer is in dilute form before it reaches the reactor.

In one preferred embodiment, the polymer concentration is kept constant in the range from 15 to 35% by weight along the reactor cascade. In another preferred embodiment, the polymer concentration is increased to from 36 to 50% by weight through the final monomer addition.

Thus, the process according to the invention for the preparation of block copolymer A is characterized by the following features:
i) a single initiation,
ii) first addition and polymerization of vinyl aromatic monomer,
iii) at least 3 times addition and polymerization of a vinyl aromatic monomer and diene mixture,
iv) second addition and polymerization of vinyl aromatic monomer, and
v) a coupling step after the addition and polymerization of the vinylaromatic monomers of the last polymer block.

The further work-up of the elastomeric block copolymer of the invention takes place by conventional processes. It is advisable here to operate in a stirred tank and, after the coupling process, optionally use a small amount of alcohol, such as isopropanol, to protonate the possible small amounts of residual carbanions and the polymer-bonded alcoholates which may have been produced in the coupling step, in order to avoid formation of deposits in the tank and discoloration of the product, and to lower the viscosity of the solution, and, prior to further work-up, to use $CO_2$/water in a conventional manner to acidify the product slightly, so that the product subsequently obtained is glass-clear with no color tinge.

It is also useful to stabilize the polymer with a free-radical scavenger or preferably with a combination of free-radical scavengers (e.g. C-free-radical scavengers, such as α-tocopherol (vitamin E), Sumilizer® GM and Sumilizer® GS and blends thereof, in combination with O-free-radical scavengers, such as Irganox® 1010, Irganox® 565 and Irganox® 1076 and blends thereof) and with a secondary oxidation inhibitor (e.g. commercially available products preferably based on phosphite, an example being triisononylphenyl phosphite (TNPP) or Irgafos® 168), and use the conventional processes to remove the solvent, and extrude and pelletize the product.

One preferred process for removing the solvent is to decrease the concentration of the solvent in stages, where, if the polymerization reaction uses a batch process, the solution is advantageously first placed into intermediate storage in a buffer tank, and then is preferably after passage through a pump heated by way of one or more heat exchangers in series to a temperature which is preferably from 100 to 140° C. above the boiling point of the solvent (this being from 180 to 220° C. in the case of cyclohexane), in order then after passage through a pressure-retention valve to be transferred via a short pipe with vapor velocities which are preferably from 100 to 350 m/s into a depressurization vessel of which the pressure and temperature are preferably adjusted in such a way that the solvent just begins to condense and the surface has a coating of a solvent film, i.e. is not dry; for cyclohexane as solvent, it is preferable here to select temperatures of from 100 to 140° C. and pressures of from 1.6 to 4.3 bar.

The solvent vapor is preferably discharged upward out of the depressurization vessel, and condensed and passed for work-up, while the polymer solution, the concentration of which is now about 70-95%, gives a precipitate in the form of flakes on the base of the vessel, from where it can be conveyed onward by way of example by a gear pump into the next heat exchanger and can be reheated, preferably to from 170 to 230° C.

The solution is then again depressurized by way of a pressure-retention valve onto the screws of a preferably twin-screw extruder, where the solvent vapor is discharged by way of vent domes upstream of and downstream of the polymer feed point. The concentration of the solvent is then preferably further reduced in extruder segments with barrier screw elements which seal against one another, while the vacuum continues to improve and upstream of the extruder head is preferably from 1 to 300 mbar, and small amounts of water are preferably injected, until the solvent content achieved is preferably <3000 ppm, particularly preferably <2000 ppm.

At the end of the extruder, the melt can be either strand-pelletized or underwater-pelletized, preference being given here to the underwater pelletization process. However, it is also possible to remove the solvent by way of other processes, for example by way of what is known as a Filmtruder in combination optionally with an extruder, or via steam stripping, as is conventional in the case of most styrene-based thermoplastic elastomers. In this case, polymer flakes are obtained. The pellets or the flakes can, like other types of rubber, be protected from adhesion by using an antiblocking agent, such as Acrawax®, Besquare®, Aerosil®, and/or tricalcium phosphate. Also dispersed oils and surfactants as processing aids, like Würtz PAT 906/EMC, in the water-circuit of the underwater granulation can help to reduce the stickiness of the granulate in the water cycle and silo.

A particular feature of the process of the invention is that the block copolymer A of the invention can be produced with good space-time yields. The space-time yield (STY) for a batch polymerization process, i.e. from the juncture at which the first monomer charge has been combined with the initiator charge until conclusion of the coupling process, i.e. the juncture at which optional addition of alcohol and evacuation of the reactor can be started, is generally from 0.5 to 3.5 h, preferably from 1 to 3 h.

Block copolymers A according to the invention are thermoplastic elastomers which are non-sticky and transparent.

Thermoplastic elastomer compositions according to the invention comprising block copolymers A are soft and can preferably be used for medical applications e.g. for tubes and infusion sets.

Component b)

Suitable plasticizers B used as component b) in the thermoplastic elastomer composition according to the invention are preferably mineral oils such as low-aromatic paraffinic oils, naphthenic oils or oligomeric polybutadienes. In particular preferred is white oil.

Other plasticizers—such as plant oils or aliphatic esters having at least 20 carbon atoms and a ratio of aliphatic C atoms to ester groups of >11, the aliphatic C atoms being the sum of the carboxylic acid component and the alcohol component—can also be used, but their use is less preferred. Among said esters diisononyl cyclohexane-1,2-dicarboxylic esters are preferred, an example being the commercially available product Hexamoll® DINCH (CAS No. Europe and Asia: 166412-78-8; CAS No. USA: 474919-59-0; from BASF SE).

The afore-mentioned plasticizers can be used alone or in combination. Preferably only one plasticizer B, in particular mineral oil, is used.

Component c)

The further additives C which can be optionally present as component c) in the thermoplastic elastomer composition according to the invention do not include plasticizers. Additives C are in particular selected from stabilizers, antiblocking agents, dyes, flame retardants, and UV absorbers.

Preferred is the use of a stabilizer, in particular oxygen radical scavengers such as Irganox® 1010 (BASF SE), Songnox® 1010, Irganox 1076, Irganox 565 and blends thereof, carbon radical scavengers such as Sumilizer® GS, Sumilizer GM and blends thereof, and/or secondary stabilizers such as Irgafos® 168 (BASF SE). Said stabilizers are commercially available. The afore-mentioned stabilizers are preferably used in amounts of 0.01 to 0.5 wt.-%, more preferably 0.1 to 0.3 wt.-%.

Further preferred is the use of antiblocking agents, such as Acrawax®, Besquare®, Aerosil®, and/or tricalcium phosphate. The afore-mentioned stabilizers are preferably used in amounts of 0.01 to 1.0 wt.-%, more preferably 0.05 to 0.5 wt.-%.

Process for the Preparation of the Thermoplastic Elastomer Composition According to the Invention The thermoplastic elastomer composition (or molding composition) according to the invention may be obtained by mixing and homogenizing the components a), b) and, if present, c) by the usual methods of plastics technology, and the sequence of adding the components may be varied. Examples of suitable mixing equipment are continuous or batch kneaders, Banbury mixers, or co-rotating or counter rotating single- or twin-screw extruders. Preferably component a) is introduced continuously into an extruder and then component b) and optionally component c) are metered in.

A further preferred variant of incorporating component b) and optional components c) into component a) is to meter component b) and optional component c) (can be used as such or in solution) into the polymer solution (e.g. in cyclohexane) of block copolymer A in the form in which it is present, for example, after the polymerization, then to homogenize the liquids, if desired, using a stirrer in a vessel or a static mixer or a combination of both, and subsequently to free the product from the solvent.

This preferred so-called impregnation variant can either be by addition of components a), b), and c) in a continuously stirred vessel or by adding the components b) and c) to a processing pipe with the solution of component a) by use of a static mixer. Components b) and c) can be added at the same time or at different stages in the process or in time (i.e. after each other in a vessel, in successive vessels, with static mixer between each addition, etc) and in all orders. Preferably, in case stabilizer additives C are used as component c), said stabilizer additives C are added before component b). Preferably, an impregnation with static mixer is used in which the stabilizer additives C are added first, followed by a static mixer, followed by the addition of component b) and finally followed by the last static mixer. Afterwards, the mixture is degassed as described for working-up below.

Depending on whether the block copolymer A has been produced in the form of flakes (as for example by steam stripping of the organic polymerization solvent), in the form of compacts, through compression of the aforementioned flakes, or in the form of pellets, by prior extrusion, different production processes for the mixtures are preferred. Flakes and compacts are preferably mixed first with the plasticizer B preferably in an apparatus which subjects the flakes to little or no shearing. This may be a rotating drum, a paddle mixer or a slow-running compounder. Suitable compounders/mixers are described in, for example, Kunststoff-Handbuch, Hanser Verlag, Munich, 1975, in Section 5.1.2.1, pages 965 to 975.

Depending on the surface nature of the flakes or of the compacts, the plasticizer B migrates into the polymer at a different rate, with a larger surface-volume ratio accelerating the incorporation. Mixing is carried out preferably until all of the oil is bound. The contact time may amount to 1 minute to 1 day, preferably 2 minutes to one hour. The temperature is preferably between 20 and 200° C., preferably between 25 and 100° C., more preferably between 30 and 50° C.

The mixture of components a) and b) is then transferred preferably to a single-screw or twin-screw or multiscrew compounder or extruder (for example, a ZSK from Coperion, formerly Werner & Pfleiderer), a BUSS kneader (Buss AG, Pratteln, Switzerland) or a LIST reactor (List AG, Arisdorf, Switzerland), and the temperature therein is raised by external heating and/or shearing to temperatures of more than 100° C., preferably more than 140° C. Suitable compounders/extruders are described in, for example, Kunststoff-Handbuch, Hanser Verlag, Munich, 1975, in Section 5.1.3.3, pages 1029 to 1091. The compounder may be fed at various points with further additives C.

If additives C are stabilizers, they need to be dosed in the above-described impregnation step (in the polymer solution).

The plasticizer B as component b) can be added at a stage as hereinbefore described but also earlier during production of component a) as dry feed on the degassing extruder.

Where the block copolymer A is in the form of pellets with a sufficient melt flow rate, it may be melted alone in an extruder and the plasticizer B may be metered in at a later point. Likewise preferred is the simultaneous metering of plasticizer B and pellets and of any further additives C (except from stabilizers).

The ready-homogenized mixture may then be worked up preferably by underwater pelletizing (hot chopping) or strand pelletizing (cold chopping), or the melt may be processed further in an injection molding machine.

Examples of further suitable continuous or discontinuous mixing elements include roll mills, Branbury kneaders, and similar elements.

Working up is accomplished preferably via multistage devolatilization with flash evaporation in the first step, the solution, prior to the evaporation, being heated in a heat exchanger to 150 to 250° C., preferably to 180 to 220° C., under superatmospheric pressure, and let down through a throttle valve preferably against pressures of between 100 mbar and 5 bar, more preferably 500 mbar to 2 bar, with the solvent, preferably cyclohexane or other hydrocarbons suitable, for example, for the anionic polymerization for preparing the block copolymers A, being very largely evaporated, preferably down to a residual amount of 1 to 20%.

The melt is preferably heated again to temperatures between 150 and 250° C. and let down again, via a pressure-maintenance valve, into a conveying element, preferably a single-screw or twin-screw or multiscrew extruder, preferably against pressures of between 500 mbar and 2 bar. The pressure can be reduced in a plurality of stages via the devolatilization domes of the extruder, down to preferably 1 to 500 mbar, preferably 5 to 400 mbar, with the temperature of the polymer melt being held preferably at between 120 and 280° C., preferably between 160 and 240° C. The melt may then be converted into pellet form by means, for example, of underwater pelletization.

Arranged at the end of the extruder, preferably, is an underwater pelletizer, also called a hot chopper, of the kind available, for example, from Gala. The residence time of the water/pellets mixture is preferably 10 seconds to 60 minutes, more preferably 2 to 15 minutes, in order to lessen the tendency of the pellets to stick. The water/pellets mixture is then separated preferably via a sieve, with the water being preferably circulated and cooled via a heat exchanger. The water preferably comprises an antiblocking agent in order to prevent the individual pellets from sticking to one another, preferably a fatty acid amide dispersion. The sieved pellets are subsequently blown dry preferably in a stream of air, and are dusted preferably with a further antiblocking agent in powder form, such as tricalcium phosphate or silica, for example. It can then be moved to a silo or packaged into sacks or other packaging means.

The thermoplastic elastomer compositions of the invention are non-sticky, soft, kink-resistant, thermoplastically processable, and readily recyclable by remelting.

Owing to the outstanding processing properties and compatibility with styrene-based thermoplastics, such as glass-clear polystyrene (GPPS), high-impact polystyrene (HIPS), styrene-butadiene block copolymers such as Styrolux® from Ineos Styrolution or K-Resin® (Ineos Styrolution), styrene-acrylonitrile polymers (SAN), acrylonitrile-butadiene-styrene polymers (ABS) or polyphenylene ethers (PPE) or GPPS/PPE mixtures, the thermoplastic elastomer compositions of the invention are appropriate for two-component {2C} injection molding or they can be easily joint just by solvent gluing.

The boundary between the afore-mentioned hard components and the thermoplastic elastomer compositions of the invention as soft components is transparent, moreover. With 2C injection molding, it is thus possible to produce flexible and rigid parts in one molding procedure. Also suitable as a hard component are polyesters such as polybutylene terephthalate, but also those with other diol components such as 1,3-propanediol, those with adipic acid, sebacic acid, succinic acid, and other aliphatic di-basic acids, including in combination with aromatic dicarboxylic acids, polycarbonate or mixtures thereof, preferably on the basis of bisphenol A.

The thermoplastic elastomer compositions are suitable for many applications in particular for producing elastic and flexible moldings and shaped articles, preferably medical articles such as infusion instruments, dialysis units, and respiration masks.

Shaped articles, in particular tubes, produced from the transparent thermoplastic elastomer compositions of the invention show an improved recovery from bending and a high wettability by water. Due to these properties it is possible to check if they are filled or contain air bubbles and to ensure an easy air bubble pass-through.

The examples below and the patent claims illustrate the invention.

EXAMPLES

Block Copolymer A

A star-shaped block copolymer A of the structure $[S_1\text{-}(S/B)_k\text{-}(S/B)_l\text{-}(S/B)_m\text{-}S_2]_n\text{-}X$ was prepared by sequential anionic polymerization of styrene (monomers S1 to S5) and butadiene (monomers B1 to B3) (cp. Table 1), and subsequent coupling using epoxidized soybean oil. 25670 ml of cyclohexane were used as initial charge (ic) and titrated to the end point with 2 ml of 1.4M sec-butyllithium (BuLi ic), and heated to 45° C. before adding 46.38 ml of a 1.4 M sec-butyllithium solution for initiation, and 5.61 ml of a 0.553 M potassium tert-amyl alcoholate (PTA) solution, as randomizer. Next, the initiator mixture was then admixed. In a next step, 1350 gram styrene (S1) was added and the polymerization reaction was allowed to run to complete monomer consumption (identified by a decrease in temperature of the reaction mixture). In a next step, 570 gram butadiene (B1) and 415 gram styrene (S2) were added simultaneously and the polymerization reaction was allowed to run to complete monomer consumption (identified by a decrease in temperature of the reaction mixture).

In a next step, again 800 gram butadiene (B2) and 720 gram styrene (S3) were added simultaneously and the polymerization reaction was allowed to run to complete monomer consumption (identified by a decrease in temperature of the reaction mixture). In a next step, again 535 gram butadiene (B3) and 310 gram styrene (S4) were added simultaneously and the polymerization reaction was allowed to run to complete monomer consumption (identified by a decrease in temperature of the reaction mixture). In a next step, 300 gram styrene (S5) was added and the polymerization reaction was allowed to run to complete monomer consumption (identified by a decrease in temperature of the reaction mixture).

Finally, 7.21 mL of Edenol® D82 dissolved in 30 mL cyclohexane was added as coupling agent and allowed to react for 10 minutes. Finally, the reaction was terminated using 0.5 ml of isopropanol and acidified with a $CO_2$ gas stream at 0.1 kg/h for 5 min and 10 mL water and a stabilizer solution (0.135 wt.-% phm* Sumilizer GS, 0.135 wt.-% phm Irganox® 1010 and 0.18 wt.-% Irgaphos 168) was added.

*phm='per hundred parts by weight of monomer' (wt.-% of component (initiator, coupling agent etc.) is calculated on the total mass of the monomers)

TABLE 1

| Block copolymer A (composition and sequence of addition) | | | | | | | | |
|---|---|---|---|---|---|---|---|---|
| | 1st block $S_1$ | 2nd block $(S/B)_k$ | | 3rd block $(S/B)_l$ | | 4th block $(S/B)_m$ | | $5^{th}$ block $S_2$ |
| SBC | S1 wt.-% | B1 wt.-% | S2 wt.-% | B2 wt.-% | S3 wt.-% | B3 wt.-% | S4 wt.-% | S5 wt.-% |
| A | 27.0 | 11.4 | 8.3 | 16.0 | 14.4 | 10.7 | 6.2 | 6.0 |

Preparation of the Thermoplastic Elastomer Composition 4 to 9 phm of mineral oil (cp. Table 2) as a plasticizer B were each added to 100 parts by weight (pbw) of the total weight of monomers used to synthesize block-copolymer A as hereinbefore described. For this purpose the plasticizer B was added to the polymer solution of block copolymer A in cyclohexane after polymerization and stabilization and before degassing, followed by 30 min of decent mixing with a propeller mixer in a vessel.

Tensile bars according to ISO 527 (1A) were produced from the obtained thermoplastic elastomer compositions for mechanical evaluation (ISO 527, cp. Table 2).

The hysteresis is measured on a tensile bar according to ISO 527 (1A). The procedure to measure hysteresis is: Stretch at 50 mm/min to 100% strain, maintain for 1 sec under constant elongation, return at 50 mm/min to zero stress, stretch at 50 mm/min to 200% strain, maintain for 1 sec under constant elongation, return at 50 mm/min to zero stress, stretch at 50 mm/min to 300% strain, maintain for 1 sec under constant elongation, return at 50 mm/min to zero stress. At this point, the elongation at zero stress is measured.

Transparency, haze and clarity were measured on a BYK Haze-gard I according to ASTM D1003 on 2 mm compression molded plates which were produced at 200° C. under 40 bar during 10 min.

TABLE 2

| Amount plasticizer B (phm) on top of 100 pbw** block copolymer A | | 4 phm | 5 phm | 6 phm | 7 phm | 8 phm | 9 phm |
|---|---|---|---|---|---|---|---|
| $M_W$ before coupling | g/mol | 96486 | 97060 | 98054 | 93142 | 92539 | 96810 |
| $M_W$ after coupling | g/mol | 258040 | 264570 | 261010 | 251770 | 246800 | 250750 |
| $MFI_{(200/5)}$ | cm³/10 min | 5.88 | 6.47 | 6.22 | 10.07 | 11.17 | 9.42 |
| Shore A | | 77.4 | 76.5 | 74.5 | 73.5 | 73.1 | 72.2 |
| Stress at break | MPa | 9.73 | 10.1 | 10.1 | 10.5 | 11.1 | 10.9 |

TABLE 2-continued

| Amount plasticizer B (phm) on top of 100 pbw** block copolymer A | | 4 phm | 5 phm | 6 phm | 7 phm | 8 phm | 9 phm |
|---|---|---|---|---|---|---|---|
| Strain at break | % | 460 | 470 | 470 | 510 | 520 | 529 |
| E Modulus | MPa | 33.0 | 27.3 | 28.8 | 23.2 | 25.9 | 24.5 |
| Hysteresis 300% | % | 58.9 | 71.5 | 62.0 | 53.4 | 57.9 | 60.2 |
| Transparency | % | 90.9 | 91.2 | 91.2 | 90.3 | 90.8 | 90.8 |
| Haze | % | 8.7 | 5 | 6.7 | 8.9 | 10 | 10.8 |
| Clarity | % | 83.8 | 86.2 | 84.9 | 81.3 | 81.6 | 80.6 |

**pbw = parts by weight

The obtained S-TPE compositions according to the invention have an improved recovery from bending which can be shown e.g. by their low hysteresis (residual strain of less than 75% at zero stress after elongation of 300% strain (cp. examples, Table 2) and the packaging test described below.

Tubes of 140 cm length produced from S-TPE compositions with 9 phm of plasticizer B were folded into length of 20 cm and stored bundled together for 1, 3 and 7 days at 20° C. The tubes were then unfolded, stretched to 150 cm for 1 second, and hung up vertically on the wall so that they could drop gravimetrically. After 30 minutes the vertically described length of each tube was measured.

The value is a measure of the recovery of the creases. The greater the value the better the recovery to the original linear shape without creases.

After hanging for 3 days, S-TPE compositions according to the invention with 9 phm of plasticizer B had a vertically described length of 127 cm whereas commercial PVC tubes taken from an intravenous set with the same outer and inner diameter had a described vertical length of 124 cm. This means that the 'bends' in the material according to the invention recover much better after unwrapping.

Furthermore, the tensile strength of the S-TPE compositions according to the invention is high as shown by a stress at break higher than 9 MPa, measured on a tensile bar according to ISO 527 (1A).

Moreover, the obtained compositions are soft, having a shore A hardness in the range of from 72.4 to 77.4.

The data as shown in Table 2 prove that the compositions according to the invention have a high transparency. Moreover, the MFI values of the inventive samples obtained are such as to allow good processing, even when increasing amounts (cp. 40, 45 phm) of plasticizer are added.

The invention claimed is:

1. A thermoplastic elastomer composition comprising components a), b), and c):
a) 97.1 to 90.9 wt.-% of at least one star-shaped block copolymer A of the structure

$[S_1\text{-}(S/B)_k\text{-}(S/B)_l\text{-}(S/B)_m\text{-}S_2]_n\text{-}X$  (I), where $S_1$ and $S_2$ are polymer blocks made from at least one vinylaromatic monomer and S/B are random copolymer blocks made from at least one vinylaromatic monomer and at least one diene forming a soft phase; X is a coupling center derived from a polyfunctional coupling agent;
b) 2.9 to 9.1 wt.-% of at least one plasticizer B; and
c) 0 to 2 wt.-% of further additives C;
wherein the sum of components a), b) and c) is 100 wt.-%;
the arms $S_1\text{-}(S/B)_k\text{-}(S/B)_l\text{-}(S/B)_m\text{-}S_2$ are identical;
the proportion of the blocks $S_1$ and $S_2$ (forming a hard phase), based on the entire block copolymer A, is from 24 to 40 wt.-%;
the vinylaromatic monomer/diene (=S/B) ratio of all of the blocks (S/B) is from 1/0.45 to 1/2.5;
the S/B-ratio of the blocks $(S/B)_k$, $(S/B)_l$ and $(S/B)_m$ is different from each other;
the S/B-ratio of the blocks $(S/B)_k$ and $(S/B)_m$ is lower than the S/B-ratio of the block(s) $(S/B)_l$;
the weight ratio of blocks S2/S1 is from 0.1 to 0.8;
the weight average molar mass $M_w$ of the block copolymer A is from 200,000 to 350,000 g/mol;
n is a natural number from 3 to 8;
k and m are each 1; and
l is a natural number of at least 1.

2. The thermoplastic elastomer composition according to claim 1 comprising components a), b), and c) in the following amounts:
a) 96.2 to 91.7 wt.-%;
b) 3.8 to 8.3 wt.-%; and
c) 0 to 2 wt.-%.

3. The thermoplastic elastomer composition according to claim 1, wherein the at least one plasticizer B is mineral oil.

4. The thermoplastic elastomer composition according to claim 1 which melt mass flow index (measured on a polymer melt at 200° C. and 5 kg load according to ISO 1133-1:2011) is in the range of from 8 to 16 cm³/10 min.

5. The thermoplastic elastomer composition according to claim 1, wherein n is a natural number from 3 to 5.

6. The thermoplastic elastomer composition according to claim 1, wherein X is a coupling center derived from epoxidized linseed oil or epoxidized soybean oil.

7. Thermoplastic elastomer composition according to claim 1, wherein $M_w$ of the block copolymer A is from 210,000 to 320,000 g/mol.

8. The thermoplastic elastomer composition according to claim 1, wherein Mw of the polymer block $S_1$ is in the range of from 18,000 to 36,000 g/mol; and Mw of the polymer block $S_2$ is in the range of from 4000 to 8100 g/mol.

9. The thermoplastic elastomer composition according to claim 1, wherein the weight ratio of blocks $S_2/S_1$ of block copolymer A is from 0.1 to 0.6.

10. The thermoplastic elastomer composition according to claim 1, wherein the S/B-ratio of the copolymer block $(S/B)_k$ is from 0.5 to 1.0; the S/B-ratio of the copolymer block(s) $(S/B)_l$ is from 0.5 to 1.2; and the S/B-ratio of the copolymer block $(S/B)_m$ is from 0.3 to 0.8.

11. The thermoplastic elastomer composition according to claim 1, wherein the weight average molar mass $M_w$ of the copolymer blocks $(S/B)_k$, $(S/B)_l$ and $(S/B)_m$ is different from each other; Mw $(S/B)_k$ is in the range of from 13,800 to 26,900 g/mol; Mw $(S/B)_l$ is in the range of from 21,200 to 41,000 g/mol; and Mw $(S/B)_m$ is in the range of from 11,500 to 23,000 g/mol.

12. A process for the preparation of a thermoplastic elastomer composition according to claim 1, wherein component a) is introduced continuously into an extruder and then component b) and optionally further components c) are metered in.

13. A process for the preparation of a thermoplastic elastomer composition according to claim 1, wherein component b) and optional component c)—as such or in solution—are added into a solution of block copolymer A, then to homogenize the liquids, and subsequently to free the product from the solvent.

14. A shaped article produced from the thermoplastic elastomer composition according to claim 1.

15. A method of using a thermoplastic elastomer composition according to claim 1 for medical applications.

16. A star-shaped block copolymer A according to claim 1.

17. A process for the preparation of block copolymer A of formula (I) according to claim 1 characterized by
  i) a single initiation,
  ii) first addition and polymerization of vinyl aromatic monomer,
  iii) at least 3 times addition and polymerization of a vinyl aromatic monomer and diene mixture,
  iv) second addition and polymerization of vinyl aromatic monomer, and
  v) a coupling step after the addition and polymerization of the vinylaromatic monomers of the last polymer block.

* * * * *